United States Patent
Phee et al.

(10) Patent No.: US 10,470,909 B2
(45) Date of Patent: Nov. 12, 2019

(54) INTRAGASTRIC DEVICE FOR WEIGHT MANAGEMENT

(71) Applicants: NANYANG TECHNOLOGICAL UNIVERSITY, Singapore (SG); NATIONAL UNIVERSITY OF SINGAPORE, Singapore (SG)

(72) Inventors: Soo Jay Louis Phee, Singapore (SG); Thanh Nho Do, Singapore (SG); Tian En Timothy Seah, Singapore (SG); Khek Yu Ho, Singapore (SG)

(73) Assignees: NANYANG TECHNOLOGICAL UNIVERSITY, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 121 days.

(21) Appl. No.: 15/749,437

(22) PCT Filed: Aug. 19, 2016

(86) PCT No.: PCT/SG2016/050402
§ 371 (c)(1),
(2) Date: Jan. 31, 2018

(87) PCT Pub. No.: WO2017/034478
PCT Pub. Date: Mar. 2, 2017

(65) Prior Publication Data
US 2018/0221185 A1 Aug. 9, 2018

(30) Foreign Application Priority Data
Aug. 21, 2015 (SG) .......................... 10201506629W

(51) Int. Cl.
*A61F 5/00* (2006.01)
*A61B 34/00* (2016.01)
*A61L 31/14* (2006.01)

(52) U.S. Cl.
CPC ............ *A61F 5/0046* (2013.01); *A61B 34/73* (2016.02); *A61F 5/003* (2013.01); *A61L 31/14* (2013.01);
(Continued)

(58) Field of Classification Search
CPC ... A61B 2034/731; A61B 34/73; A61F 5/003; A61F 5/0033; A61F 5/0046; A61L 31/14
See application file for complete search history.

(56) References Cited

U.S. PATENT DOCUMENTS

2011/0022072 A1* 1/2011 Marco ...................... A61F 2/02
606/192
2013/0138132 A1* 5/2013 Phee ..................... A61F 5/0046
606/192

FOREIGN PATENT DOCUMENTS

CN 105250060 A 1/2016
CN 205041579 U 2/2016
(Continued)

OTHER PUBLICATIONS

Foreign Communication from a Related Counterpart Application, International Search Report and Written Opinion dated Nov. 10, 2016, International Application No. PCT/SG2016/050402, filed on Aug. 19, 2016.
(Continued)

*Primary Examiner* — Todd J Scherbel
*Assistant Examiner* — Brooke Labranche

(57) ABSTRACT

An intragastric device comprising: an inflation magnet provided within a capsule and configured to move towards a first end of a capsule during activation of the intragastric device by applying a magnetic field externally to a user after swallowing the intragastric device; a first chamber and a second chamber physically separated by a partition having a through hole; a separator connected to the inflation magnet and sealing the through hole before activation of the intra-
(Continued)

gastric device, wherein activation of the intragastric device moves the separator to unseal the through hole to allow a chemical reaction between a first chemical stored in the first chamber and a second chemical stored in the second chamber; a balloon secured to the capsule and collapsed against the capsule before activation of the intragastric device; and an expandable volume configured to expand when the balloon is inflated by a gaseous product of the chemical reaction.

20 Claims, 8 Drawing Sheets

(52) U.S. Cl.
CPC ....... *A61B 2034/731* (2016.02); *A61F 5/0033* (2013.01)

(56) References Cited

FOREIGN PATENT DOCUMENTS

| | | |
|---|---|---|
| WO | WO2011136745 A1 | 11/2011 |
| WO | WO2017034478 A1 | 3/2017 |

OTHER PUBLICATIONS

Do, Thanh Nho, et al., Development and Testing of a Magnetically Actuated Capsule Endoscopy for Obesity Treatment. PLOS One, Jan. 27, 2016, vol. 11, No. 1, pp. e0148035:1-23 [Retrieved on Oct. 19, 2016-] DOI: 10.1371/Journal.Pone.0148035 whole document, esp. figures 2, 5-7; section of Materials and Methods.

\* cited by examiner

INTRAGASTRIC DEVICE FOR WEIGHT MANAGEMENT

CROSS-REFERENCE TO RELATED APPLICATIONS

This application is a filing under 35 U.S.C. 371 as the National Stage of International Application No. PCT/SG2016/050402, filed Aug. 19, 2016, entitled "INTRAGASTRIC DEVICE FOR WEIGHT MANAGEMENT," and which claims the benefit of and priority to Singapore Application No. 10201506629W, filed with the Intellectual Property Office of Singapore on Aug. 21, 2015, both of which are incorporated herein by reference in their entirety for all purposes.

FIELD

This invention relates to an intragastric device for weight management.

BACKGROUND

Obesity is a condition when the accumulated body weight of a person is above a certain threshold that may give rise to negative health issues such as increased chances of diabetes, cardiovascular diseases, musculoskeletal disorders, and even cancer. This happens when the intake of food is higher than the output of energy in the form of physical activities. According to a report from the World Health Organization, the number of obese people worldwide has doubled since 1980. In 2008, adults aged 20 and above worldwide were 35% overweight and 11% obese. This number is expected to grow annually. Definitely, the best way to address problems caused by obesity is to prevent it. Nevertheless, due to modernization and change in working patterns, maintaining a balanced diet and taking regular exercise become more challenging. Adults tend to consume high-calorie food in a larger quantity while leading a sedentary lifestyle, thus increasing chances of obesity.

Currently, various options are available on the market to promote weight loss for adults. Over-the-counter slimming herbs, anti-obesity drugs, body sculpting and weight management programs promise undeliverable and non-sustainable results with various mild and adverse side effects. For individuals with more severe obesity, medical procedures such as the bariatric surgery and placement of gastric balloons are available.

Bariatric surgery involves manual alteration of the stomach size or the digestive track by means of gastric bypass or by using gastric bands. These procedures are proven to be effective in promoting weight loss, but they are invasive and may cause adverse effects such as surgical complications, metabolic bone diseases, and kidney diseases.

Introducing a gastric balloon to occupy stomach space and hence reduce gastric volume and improve satiety [1] is less invasive than bariatric surgery. The first intra-gastric balloon (IGB) that was commercialized is the Garren-Edwards Gastric Bubble (GEGB) [2] in 1985. Since then, several different IGBs have been developed and some remain currently available on the market [3][4]. Although IGBs produced initial high efficacy in some clinical reports [5], effectiveness in reducing weight in the long run is decreased as prolonged use results in gastric accommodation and loss of satiety effects. Furthermore, currently available IGBs require placement and removal via methods that give rise to patient discomfort and possible complications. Due to these limitations, IGBs remain as a second choice modality for patients who are not fit for surgery or for the super obese who may require modest weight loss prior to other intervention, and are still not widely accepted as a generic weight-loss solution despite their known efficacy in promoting weight loss.

SUMMARY

The presently disclosed intragastric device is self-contained, requiring no physical connection to external devices. It also contains no on-board electronics, allowing it to be small enough for oral administration. This removes the need for surgical implantation or other complex gastric procedures and means that the patient experiences less discomfort when swallowing it as does not make use of tubes trailing out of oesophagus and nasal/oral cavity for inflation. This further reduces patient discomfort, potentially increasing its uptake.

Its position in the stomach is confirmed by radiofrequency detectors or magnetic hall effect sensor network, and inflation is an on-demand, remotely triggered 1-step process. For safety, both automated and optionally manual deflation methods may be incorporated into the capsule. Manual deflation, if provided, is a similarly uncomplicated 1-step process.

The non-invasive method of administration eliminates hospitalisation and reduces recovery time, and allows it to be administered more conveniently and frequently. The shorter treatment cycle results in fewer problems with gastric accommodation and thus increases its overall efficacy. The automatic and optional manual deflation features make it less likely to obstruct the alimentary canal for long periods of time, enhancing safety. The low cost of the materials involved and ease of use mean that it can also be sold more cheaply than existing commercial solutions.

The intragastric device comprises a self-contained ingestible weight management pill in the form of an elongated capsule with a longitudinal axis with an inflatable membrane or balloon encompassing at least a portion of the capsule. The device has a separator dividing two chambers and each chamber containing a different chemical that reacts to produce a gas when mixed together. The chemicals are brought into contact with one another by an inflation magnetically induced configuration change which removes the separator and allowing the chemicals to mix, which in turn, generates a gas to inflate the membrane or balloon. The inflated membrane or balloon will occupy more space in the stomach and this induces the feeling of satiety in the patient taking the pill.

The position of the device within the digestive tract may be determined by using externally located Hall Effect sensors to track the inflation magnetic signature of the device. Alternatively, radio frequency identification capabilities could be incorporated into the device and detected when in proximity to an external radiofrequency identity (RFID) sensor. The external inflation magnetic field may also be able to provide a locomotive force to the device in the desired direction so as to position it for expansion or drug release.

The mechanism for the inflation subcomponent is located entirely within the device (in the form of a capsule). Inflation is achieved by having a chemical reaction take place when two or more chemicals (liquid or solid based) are mixed together. Prior to the mixing, the chemicals are physically separated by a separator and the mixing is magnetically triggered when the separator is removed. This may be achieved by having the separator being part of a partition to separate the internal volume of the device into two separate compartments and each compartment containing one of the chemicals. The separator is coupled to a slidable inflation magnet within the capsule which is configured to move axially towards the distal or first end of the capsule when an external inflation magnetic force with a specific inflation magnetic field flux is brought into close proximity. The movement of the inflation magnet that is coupled to the separator correspondingly pulls the separator and the partition apart, allowing the two chemicals, (where one or both are in solute/solid form) to mix and react with one another, thus generating a gas.

For safety, the reactants should be biocompatible or at a concentration low enough to be rendered harmless upon leakage of the device.

The gas generated will result in the inflation of an elastic outer wrapping (balloon). However it could also be a prior well-packaged internal membrane that is inflated by the gas pressure. This material should be biocompatible and be able to resist degradation by the naturally produced gastrointestinal fluids until its function has been fulfilled.

The device may include a deflation mechanism that allows the device to be automatically or manually deflated. This allows the device to pass safely through the digestive tract and be evacuated. In an automated method, the permeability of the wrapping membrane to the inflation gas can be altered to make it last a required length of time. Alternatively, the membrane/balloon or other parts could be chemically degraded over time.

For optional manual deflation, the device may include a secondary inflation magnetically actuated mechanism, similar to that of inflation, but triggered by an exact opposite external inflation magnetic field. In other words, the actuation/triggering mechanism for actuation and deflation may be differentiated by the direction of inflation magnetic field applied. The direction of the applied inflation magnetic field may thus determine which of the actuating mechanisms is triggered.

In another embodiment, the device may contain pharmaceutical drugs and the external inflation magnetic force or pressure from a chemical reaction may cause them to exit the device and provide therapy to areas of the alimentary canal.

In another embodiment, the device may provide an inflation magnetically actuated means of collecting tissue samples for biopsy.

According to a first aspect, there is provided an intragastric device for weight management, the intragastric device comprising:
a capsule having a longitudinal axis, the capsule configured to be readily swallowed by a human person;
an inflation magnet provided within the capsule such that one of a north pole and a south pole of the inflation magnet is facing a first end of the capsule, the inflation magnet being displaced from the first end of the capsule, the inflation magnet configured to slideably engage the capsule during movement of the inflation magnet along the longitudinal axis, the inflation magnet configured to move towards the first end of the capsule during activation of the intragastric device by application of an inflation magnetic field externally to a user after the intragastric device has been swallowed by the user;
a first chamber configured to store a first chemical therein;
a second chamber configured to store a second chemical therein;
a partition configured to physically separate the first chamber from the second chamber, the partition having a through hole, the inflation magnet provided between the partition and the first end of the capsule, the first chamber defined within the capsule at least partially between the inflation magnet and the partition, the second chamber defined at least partially by the partition and the capsule;
a separator sealing the through hole in the partition before activation of the intragastric device, the separator being connected to the inflation magnet wherein movement of the inflation magnet towards the first end of the capsule moves the separator to unseal the through hole;
wherein fluid communication is established between the first chamber and the second chamber via the through hole when the through hole is unsealed to allow a chemical reaction between the first chemical and the second chemical;
a balloon secured to the capsule and collapsed against an outer surface of the capsule before activation of the intragastric device; and
an expandable volume defined at least partially by the balloon and the outer surface of the capsule, the expandable volume configured to expand when the balloon is inflated by a gaseous product of the chemical reaction.

The second chamber and the expandable volume may be one and the same.

The partition may comprise the second end of the capsule. Alternatively, the partition may comprise a side wall of the capsule.

The first chamber may comprise a first portion defined between the inflation magnet and the partition and a second portion defined between the partition and a second end of the capsule, wherein the partition comprises a first layer having a first opening and a second layer having a second opening, the first opening and the second opening defining the through hole of the partition, the first layer and the second layer being spaced apart and defining a channel therebetween, the channel being in fluid communication with the second chamber via a channel opening in a side wall of the capsule.

The second chamber may be defined within the capsule between the partition and a second end of the capsule, and ventilation holes are provided in the capsule to establish fluid communication between the second chamber and the volume.

A deflation valve may be provided at the second end of the capsule, the deflation valve allowing passage of the gaseous product out of the balloon.

The deflation valve may comprise a through opening in the second end of the capsule and a plug sealing the through opening before deflation of the intragastric device, the intragastric device further comprising a deflation magnet provided within the capsule and oriented in a same direction as the inflation magnet, the deflation magnet being displaced from the second end of the capsule, the deflation magnet configured to slideably engage the capsule during movement of the deflation magnet along the longitudinal axis, the deflation magnet configured to move towards the second end of the capsule during application of an inflation magnetic field externally to the user wherein movement of the deflation magnet causes removal of the plug from the through opening.

The deflation magnet may be connected to the plug via a flexible cable run over a pulley provided in the capsule, wherein movement of the deflation magnet towards the second end of the capsule pulls the plug into the capsule to unseal the through opening.

The deflation magnet may be provided with a bar extending towards the second end of the capsule, wherein movement of the deflation magnet towards the second end of the capsule results in the bar coming into contact with the plug and pushing the plug out of the capsule to unseal the through opening.

The intragastric device may further comprise retaining stubs projecting from an inner surface of the capsule, the retaining stubs limiting extent of movement of the inflation magnet towards a second end of the capsule.

The inflation magnet may be connected to the separator via one of: a rigid rod and a flexible wire.

The intragastric device may further comprise a flexible membrane provided in the capsule between the inflation magnet and the first chamber, a perimeter of the flexible membrane sealed with the capsule.

The flexible membrane may be connected to the inflation magnet via a biodegradable connector.

A portion of the capsule containing the inflation magnet may be connected to the rest of the capsule via a biodegradable ring, wherein the inflation magnet and the portion of the capsule containing the inflation magnet become detached from the rest of the capsule upon biodegradation of the biodegradable connector and the biodegradable ring.

The separator may be connected to the inflation magnet via an adhesive connection to the flexible membrane.

The flexible membrane may allow passage of the gaseous product out of the balloon over time.

The balloon may allow passage of the gaseous product out of the balloon over time.

The balloon may comprise a deflation valve allowing passage of the gaseous product out of the balloon over time.

The separator may be configured to reseal the through hole in the partition when the externally applied inflation magnetic field is removed.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

DETAILED DESCRIPTION

Figure 1:
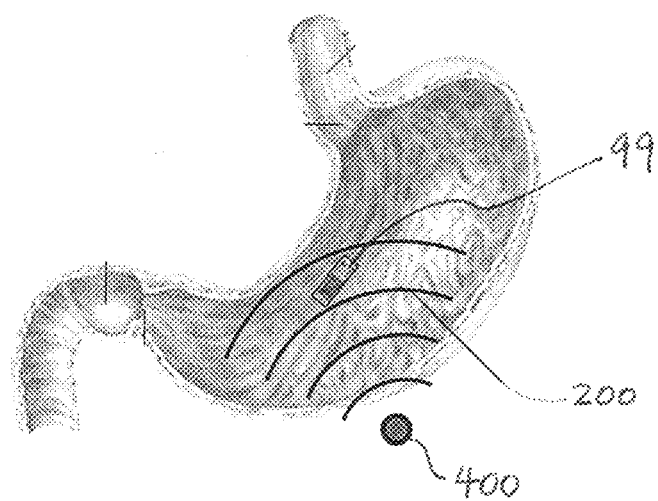
FIG. 1 is a schematic illustration showing RFID detection of location of the intragastric device in the stomach.
Figure 2:
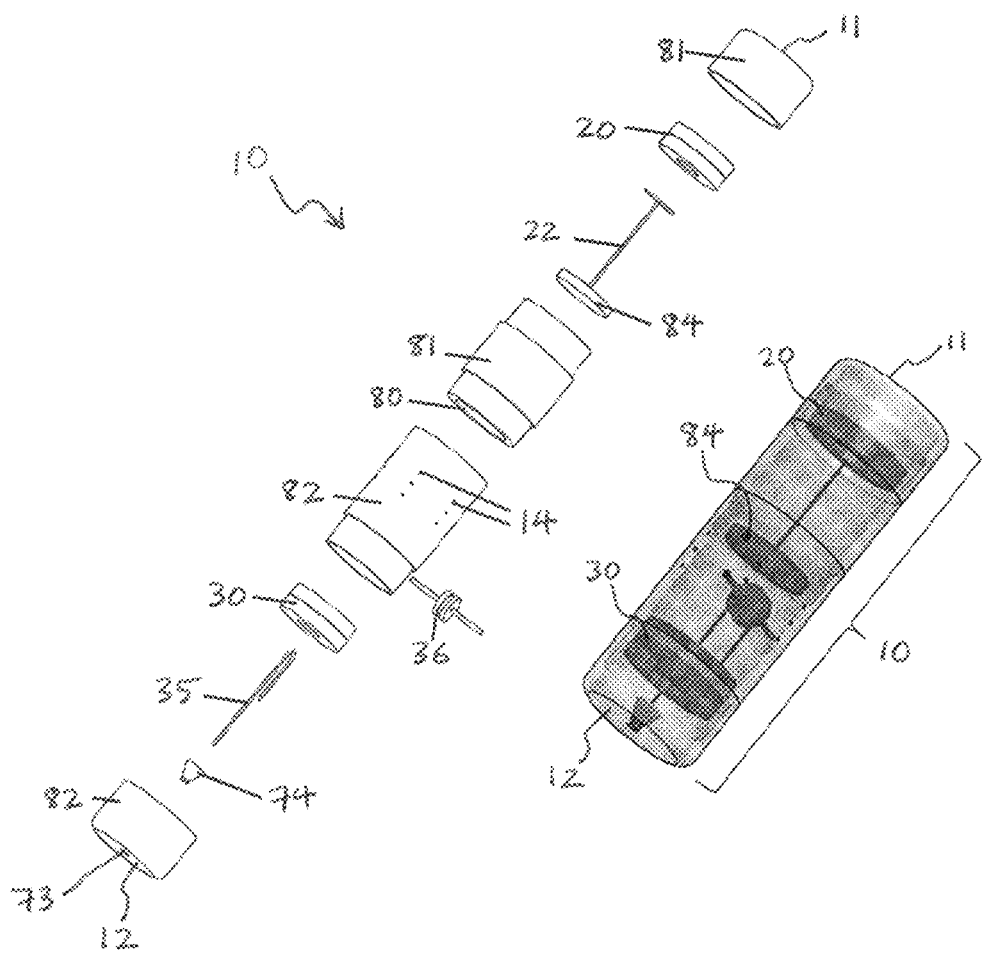
FIG. 2 is an exploded assembly view and perspective view of a first embodiment of a capsule of the intragastric device.
Figure 3:
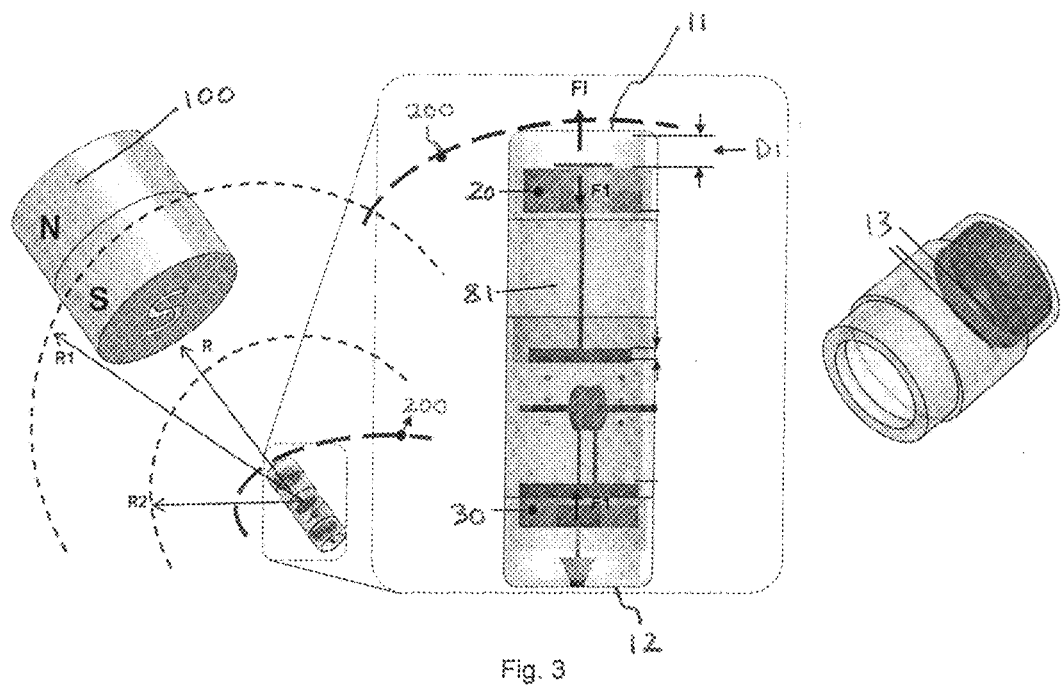
FIG. 3 is a schematic illustration of use of an external magnet to inflate the intragastric device in the stomach.

Exemplary embodiments of the intragastric device 99 for weight management will be described below with reference to FIGS. 1 to 21. The same reference numerals are used throughout the figures to denote the same or similar parts among the various embodiments.

Location

The preferred embodiment of the intragastric device 99 possesses a number of strong internal inflation magnets, the number of inflation magnets being at least one. The intragastric device 99 can be located after ingestion by means of a Hall effect sensor network or RFID, as shown in FIG. 1. Detectors are preferably located just outside the patient near his/her stomach 200. The detectors 400 are positioned to cover all possible loci bounded by the lower oesophageal sphincter and the pyloric sphincter. X-rays may also be used to confirm the position of the intragastric device 99 as the inflation magnets are strongly radiopaque. The strong inflation magnetism allows the intragastric device 99 to be actuated even when its determined position has a few centimetres of error, for example in intragastric applications where the intragastric device 99 may be floating around in the stomach fluids. The externally applied inflation magnetic field relies on a strength gradient to direct the intragastric device 99 such that it can be braced against a resistant tissue surface. This reaction force from the resistant surface, opposite to the net inflation magnetic force on the intragastric device 99, also causes the inflation mechanism to be activated, as will be described in greater detail below. The external inflation magnetic field may be generated by a large permanent inflation magnet or solenoid. Other embodiments may utilise Helmholtz coils or Gauss coils to generate the inflation magnetic gradient. Once the field strength at the location of the intragastric device 99 exceeds a certain value, either by increasing the power supplied to the electroinflation magnetic apparatus or by moving the permanent inflation magnet closer to the intragastric device 99, the inflation mechanism is triggered. However, in order to prevent injury to the patient, the force exerted by the intragastric device 99 on the gastric wall cannot be too great.

Structure

For all embodiments of the intragastric device 99, including the exemplary embodiments described below, the intragastric device 99 inflation magnetic weight-loss capsule includes a number of components. Among the components are an inner capsule 10 having a longitudinal axis X, the capsule 10 configured to be readily swallowed by a human person. The capsule 10 is preferably made wholly or in part of moulded plastic or gelatin. The capsule 10 is preferably cylindrically shaped. This shape allows minimal patient discomfort when swallowing. The maximum diameter of the capsule 10 should be less than the minimum width of the oesophagus. The capsule 10 is made from biocompatible and acid resistant materials such as PDMS.

Figures 17, 18:
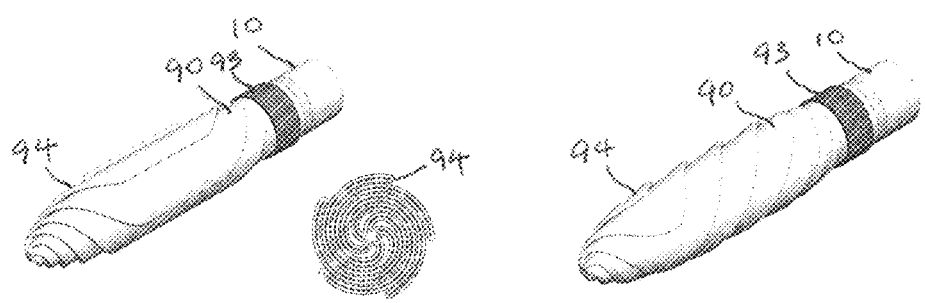
FIG. 17 is a perspective view of the folded balloon on the capsule.
FIG. 18 is a perspective view of the twisted balloon on the capsule.
Figures 19, 20:
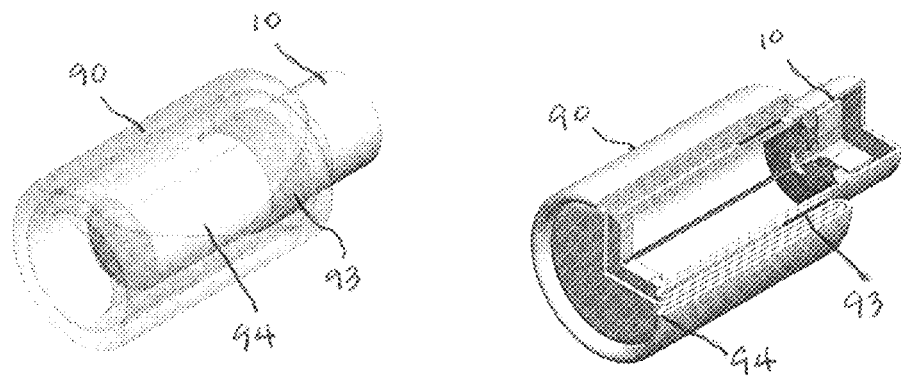
FIG. 19 is a perspective view of the balloon scrolled on the capsule.
FIG. 20 is a perspective view of the balloon concentrically folded on the capsule.
Figure 21:
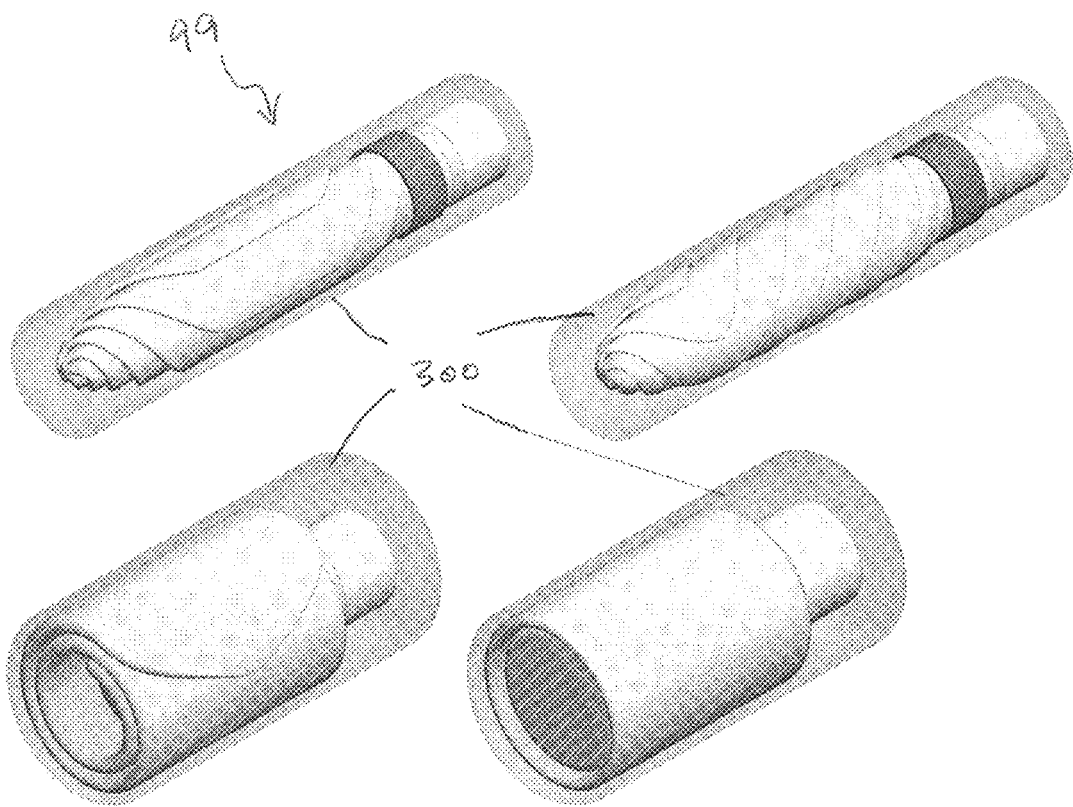
FIG. 21 is perspective views of a cover on various embodiments of the intragastric device.

A membrane or balloon 90 (not shown in FIG. 2) is secured 93 to the capsule 10 and provided in a collapsed state against an outer surface 19 of the capsule 10 before activation of the intragastric device 99. An adhesive silicone rubber such as PDMS 93 may be used to seal the balloon 90 to the capsule 10, or alternatively, the glue 93 used to seal the balloon 90 to the capsule 10 could be chemically degradable. An expandable volume 98 defined at least partially by the balloon 90 and the outer surface 19 of the capsule 10 is configured to expand when the balloon 90 is inflated. Upon inflation, the balloon 90 expands into a spheroid volume. The balloon 90 is preferably made of an elastic material such as silicone or rubber. In its initial state, the balloon 90 is wrapped, folded or otherwise collapsed against the outside 19 of the capsule 10. Embodiments of the collapsed balloon are shown in FIGS. 17 to 20 in which the balloon 90 may be folded or twisted to form pleats 94 as shown in FIGS. 17 and 18, or the balloon 90 may be scrolled around the capsule 10 as shown in FIG. 19 or folded concentrically around the capsule 10 as shown in FIG. 20. A weak binding/covering or coating 300 made of a biodegradable material such as chitosan or gelation or a combination between chitosan and PDMS provided around the balloon 90 and the capsule 10 as shown in FIG. 21 is preferably used to keep the balloon 90 collapsed and to facilitate passage of the intragastric device 99 down the oesophagus when the intragastric device 99 is being swallowed by the user. This covering is configured to be dissolved in the gastric acid environment a few hours after the intrastric device 99 has been swallowed. The balloon 90 is designed to retain at least 60% of its volume up to a period of at least 30 days.

The membrane or balloon 90 may have elastic properties, which allows it to accommodate inexact quantities of gas produced whilst maintaining a desired shape. However, the membrane or balloon 90 cannot be made of too compliant a material, to avoid it getting sucked into the sphincter of the user. Its shape and size should also resist passage through the pyloric sphincter and preclude blockage of the sphincter. A simple spheroid shape may suffice, since the volume occupying subcomponent is expected to be buoyant and thus reside on the surface of the gastric juices, away from the pyloric sphincter. Other possible shapes include a toroid, which has a hole in the middle to allow partially digested food to pass through the sphincter.

The material of the membrane or balloon 90 may be designed to fail after a certain time of residence in the stomach. A possible embodiment of the membrane or balloon 90 may consist of multiple layers of varying gas permeability properties and resistance to chemical degradation, such that the rate of escape of gas is low initially but increases exponentially once the impermeable but degradable layer has been dissolved. Dissolution may be initiated by either residual chemicals within the device, which may be activated as part of the manual deflation method outlined in the deflation subcomponent, or it may be caused by the gastric juices in the stomach.

The inflation mechanism of the intragastric device 99 is designed to be entirely physically self-contained within the device 99, such that the patient does not need to ingest anything else. Inflation is triggered remotely by an external inflation magnetic force once residence of the intragastric device 99 in the stomach has been confirmed by the physician. This avoids premature inflation of the device 99 while in the oesophagus or delayed inflation of the device 99 when it has already passed into the small intestine.

Volume of the intragastric device 99 is increased by a gas-generating chemical reaction. Possible reactions include the reaction of an acid and a base to produce carbon dioxide gas, or a catalyst induced decomposition of hydrogen peroxide into oxygen and water. Chemicals involved in these reactions have to be housed separately prior to the swallowing of the device 99, which can be accomplished by means of a septum or partition 80 provided in the device 99. To that end, before use, a first chemical such as a liquid reactant A is stored inside the capsule 10 in a first chamber 81 of the intragastric device 99. A second chemical such as a powdered solid reactant B is stored in a second chamber 82 of the intragastric device 99. The two chambers 81, 82 are separated by the septum or partition 80. The partition 80 has a through hole 83. A separator 84 such as a compliant silicone element that may be shaped as a disk or truncated cone seals the through hole 83 before use of the intragastric device 99. The second chamber 82 is defined at least partially by the partition 90 and the capsule 10, and may be either wholly inside the capsule 10 as shown in FIGS. 2 to 4, 7 and 8(a) or outside the capsule 10 as shown in FIGS. 5, 8(b), 9 to 12, 14 and 15. An RFID chip and antenna are preferably integrated into the side of the capsule 10.

The first chamber 81 is configured to contain aqueous solution of acid, for example citric acid or acetic acid, and is preferably made of an inert plastics or rubber material. All mechanisms in contact with the liquid in the first chamber 81 should have been treated to be similarly inert.

The second chamber 82 preferably contains some or all of the second chemical B, such as potassium bicarbonate powder or bicarbonate powder.

An inflation magnet 20 is provided within the capsule 10 such that either a north pole N or a south pole S of the inflation magnet 20 is facing the top or first end 11 of the capsule 10. The orientation of the inflation magnet determines the activating inflation magnet polarity for triggering chemical mixing. The inflation magnet 20 is displaced by a distance D1 from the first end 11 of the capsule 10 and configured to slideably engage the capsule 10 during movement of the inflation magnet 20 along the longitudinal axis X. Sufficient gap exists between the inflation magnet 20 and the first end 11 of the capsule 10 so as to allow motion of the inflation magnet 20 and its connected components along the longitudinal axis X of the capsule 10. Retaining stubs 13 are moulded into an inner surface 18 of the capsule 10 to limit the axial extent of motion of the inflation magnet 20. Initially, before use, the inflation magnet 20 rests against the retaining stubs 13 and the separator 84 or silicone element forms part of the septum or partition 80 to seal the through hole 83, creating a watertight seal. The inflation magnet 20 can be a type of ring magnet, cylinder magnet or spherical magnet.

The inflation magnet 20 is configured to move towards the first end 11 of the capsule 10 during activation of the intragastric device 99 by application of an inflation magnetic field externally to a user after the intragastric device 10 has been swallowed by the user. The inflation magnet 20 is preferably a cylindrical neodymium inflation magnet with a central hole. The inflation magnet 20 may be Teflon coated for chemical inertness and ease of sliding inside the capsule 10.

The inflation magnet 20 is thus provided between the partition 80 and the first end 11 of the capsule 10, so that the first chamber 81 is defined within the capsule 10 at least partially between the inflation magnet 20 and the partition 80. The balloon 90 is preferably sealed to the outside 19 of the capsule 10 adjacent the end of the first chamber 81 that is nearest the inflation magnet 20.

The separator 84 is connected by a connector 22 comprising either a rigid bar or flexible wire 22 to the inflation magnet 20 so that movement of the inflation magnet 20 towards the first end 11 of the capsule 10 moves the separator 84 to unseal the through hole 83. The connector 22 should be acid resistant.

Inflation

Figure 4:
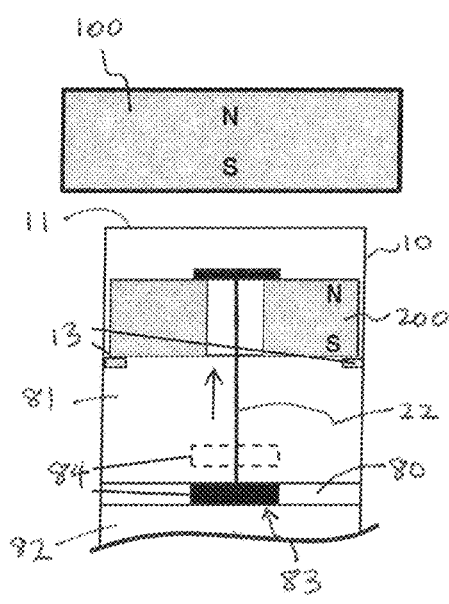
FIG. 4 is a schematic cross sectional view of a first exemplary embodiment of the intragastric device.

After entry of the capsule 10 into the stomach is confirmed, the positioning detector(s) are withdrawn and an external inflation magnet 100 is gradually brought closer to the stomach, leading with its south pole. With reference to FIG. 4, let R be the distance measured from the free-floating capsule 10 to the external inflation magnet 100 When R falls below R1, the inflation magnetic force exerted on the capsule 10 will cause it to move towards and align itself in the same North-South orientation as the external inflation magnet. This will cause the first end 11 of the capsule 10 to be braced against the inner lining of the stomach. If R is now less than R2, the force on the inflation magnet 20 will overcome the frictional force between the silicone element or separator 84 and the rest of the septum wall or partition 80. If R has not yet decreased below R2, the external magnet 100 continues to approach the stomach wall anyway, until R<R2. The inflation magnetic force causes the inflation magnet 20 and the silicone element or separator 84 to move axially, breaking the seal to open the through hole 83, thereby releasing the first chemical such as citric acid from the liquid containing first chamber 81 into the powder containing second chamber 82.

The powder containing second chamber 82 is designed to hold enough second chemical such as a base, such that the balloon 90 attains at least 50% of its occupied volume within 10 minutes of reaction time. This is to prevent evacuation of the device 99 through the pyloric sphincter, which happens to large food particles after 15 minutes. 90% inflation of the balloon 90 will occur over a longer time frame of up to 6 hours, as it will be dependent on the normal motility of the patient post-administration to make the remaining first chemical (e.g. acid) in the first chamber 81 come into contact with the second chemical (base powder) in the second chamber 82.

Exemplary Embodiment 1

In a first embodiment as shown in FIGS. 2 to 4, 6(*a*) and 7, the powder or second chamber 82 is defined within the capsule 10 between the partition 80 and a second end 12 of the capsule 10. Ventilation holes 14 are provided in the side walls 15 of the capsule 10 to establish fluid communication between the second chamber 82 and the volume 98 in the balloon 90. The ventilation holes 14 of the second chamber allow a gaseous product of the chemical reaction between the first chemical A and the second chemical B to inflate the balloon. For example, an acid-base reaction where the first chemical A is the aqueous acid and the second chemical B is bicarbonate powder would produce $CO_2$ gas. The powder in the second chamber 82 is preferably compacted to reduce its volume and to minimise its migration out of the ventilation holes.

In this embodiment, during the chemical reaction, acid will be ejected by the evolved gas such as carbon dioxide out of the ventilation holes 14. Unreacted first chemical such as acid solution in the reaction or second chamber 82 may also leak out over time through the ventilation holes 14. Thus, in this embodiment, the folded balloon membrane 90 may also contain some of the second chemical (e.g. base) before use, to react with the first chemical (e.g. defenestrated acid).

Exemplary Embodiment 2

Figure 5:
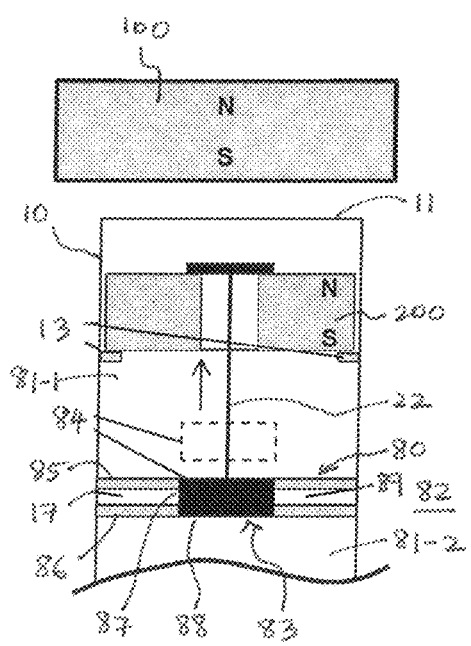
FIG. 5 is a schematic cross sectional view of a second exemplary embodiment of the intragastric device.

In a second exemplary embodiment as shown in FIG. 5, the second chamber 82 and the expandable volume 98 are one and the same. In other words, the expandable volume 98 in the balloon 90 serves as the second chamber 82 to store the second chemical prior to mixing of the first and second chemicals. In this embodiment, the first chamber 81 comprises a first portion 81-1 defined between the inflation magnet 20 and the partition 80, and a second portion 81-2 defined between the partition 80 and a second end 12 (not shown in FIG. 6) of the capsule 10. In this embodiment, the partition 80 comprises a first layer 85 having a first opening 87 and a second layer 86 having a second opening 88. The first opening 87 and the second opening 88 define the through hole 83 of the partition 80, and are both sealed by the separator 84 before use of the device 99. The first layer 85 and the second layer 86 are spaced apart to define a channel 89 there between. The channel 89 is in fluid communication with the second chamber 82, 98 via one or more channel openings 17 in the side wall 15 of the capsule 10.

When the first and second openings 87, 88 are unsealed by the separator 84 moving away from the through hole 83 (to an open position as indicated by the dotted lines in FIG. 5) as a result of the inflation magnet 20 being attracted towards the first end 11 of the capsule 10 by the external magnet 100, the channel 89 comes into fluid communication with both the first portion 81-1 and second portion 81-2 of the first chamber 81. As the channel 89 is already in fluid communication with the second chamber 82, 89, this allows the first chemical stored in both the first portion 81-1 and second portion 81-2 of the first chamber 81 to mix with the second chemical in the second chamber 82, 89 to produce the gas to inflate the balloon 90.

Deflation Mechanism With Deflation Magnet

In the first and second exemplary embodiments described above with reference to FIGS. 2 to 5, a deflation mechanism as shown in FIGS. 6(*a*) and 6(*b*) may be provided. The deflation mechanism comprises a deflation magnet 30 provided within the capsule 10 such that a north pole N and a south pole S of the deflation magnet 30 are oriented in the same direction as that of the inflation magnet 20. In one example, the inflation magnet 20 is oriented with its north pole N facing the first end 11 of the capsule 10. Accordingly, the deflation magnet 30 is oriented with its north pole N facing the first end 11 of the capsule 10 so that the south pole S of the deflation magnet 30 faces the second end 12 of the capsule 10.

The deflation magnet 30 is preferably another cylindrical neodymium inflation magnet. Retaining stubs 16 provided on the inner surface 18 of the capsule 10 constrain the initial position of the deflation magnet 30. A small attractive force will exist between the inflation magnet 20 and the deflation magnet 30, holding them in place during transport and ingestion of the capsule 10, thus preventing accidental activation of the mechanisms. There is an air gap of displacement D2 between the deflation magnet 30 and the bottom or second end 12 of the chamber 10 as the deflation magnet 30 is displaced from the second end 12 of the capsule 10 before use by the retaining stubs 16, which allows motion of the deflation magnet downwards or towards the second end 12 of the chamber 10.

The second end 12 of the chamber contains a hole or through opening 73 that is stoppered by a plug 74 that is preferably made of silicone before deflation of the intragastric device 99. The plug 74 is either pulled (FIG. 6(a)) or pushed (FIG. 6(b)) out of the through opening 73 by the movement of the deflation magnet 30 towards the distal tip or second end 12 of the capsule 10. The deflation magnet 30 is configured to slideably engage the capsule 10 during movement of the deflation magnet 30 along the longitudinal axis X, the deflation magnet 30 configured to move towards the second end 12 of the capsule 10 during application of an inflation magnetic field externally to the user wherein movement of the deflation magnet 30 causes removal of the plug 74 from the through opening 73.

Figures 6A, 6B:
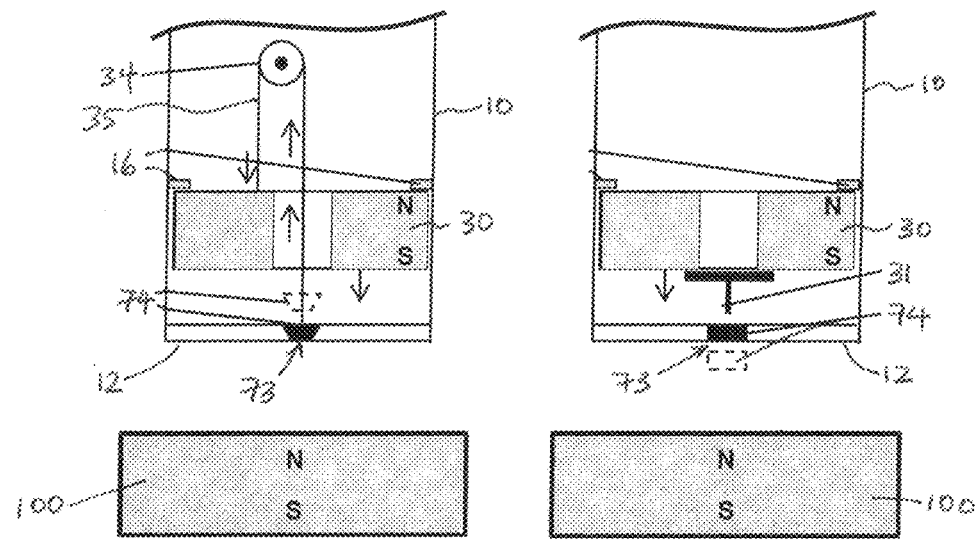
FIG. 6(a) is a schematic cross sectional view of a first exemplary embodiment of a deflation mechanism of the intragastric device.
FIG. 6(b) is a schematic cross sectional view of a second exemplary embodiment of a deflation mechanism of the intragastric device.
Figure 7:
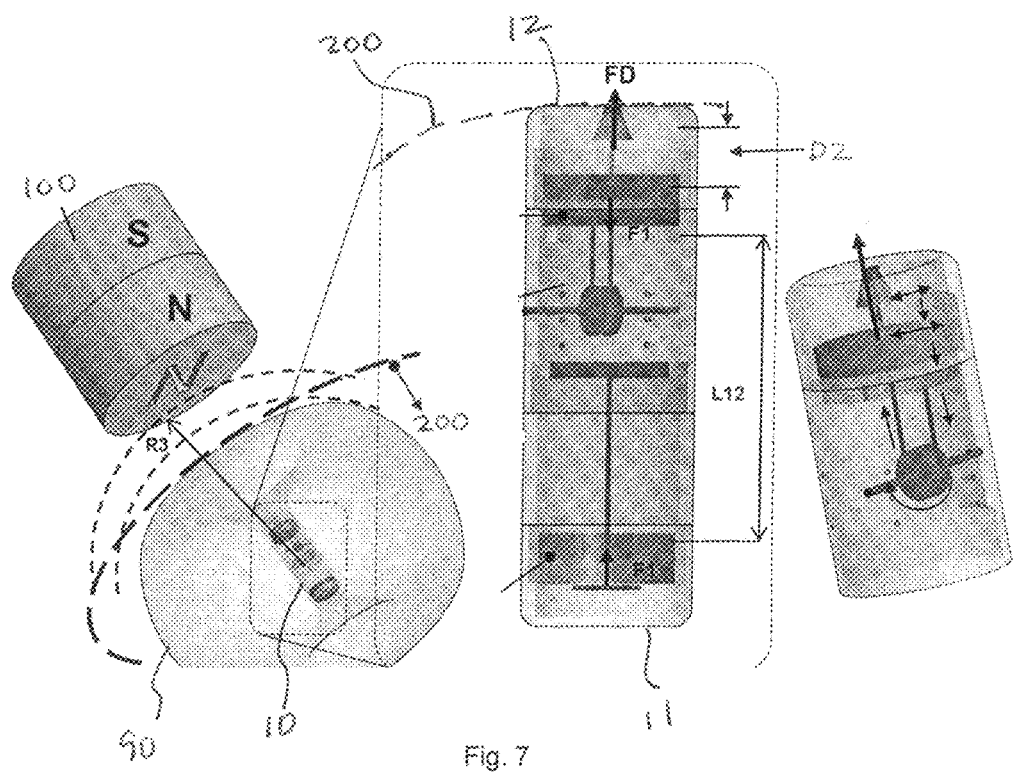
FIG. 7 is a schematic illustration of use of an external magnet to deflate the intragastric device in the stomach.

Two possible embodiments of mechanically coupling the deflation magnet 30 to the plug 74 are shown in FIGS. 6(a) and (b). In the first (FIG. 6(b)), the deflation magnet 30 has a protrusion or bar 31 extending towards the second end 12 of the capsule 10, wherein movement of the deflation magnet 30 towards the second end 12 of the capsule 10 results in the bar 31 coming into contact with the plug 74 and pushing the plug 74 out of the capsule 10 to unseal the through opening 73.

In the second (FIG. 2, 3, 6(a), 7), the silicone plug 74 is connected to the deflation magnet 30 by a flexible wire/thread or cable 35 and pulley 36 system in which the cable 35 is run over the pulley 36 provided in the capsule 10. The plug 84 is pulled inward and retained in the capsule 10 to unseal the through opening 73 when the deflation magnet 30 is moved towards the second end 12 of the capsule 10. The plug 74 is preferably conical shaped to resist being pushed out of the capsule 10 by the internal air pressure of the balloon 10.

In the deflation process, the presence of the device 99 inside the stomach is first confirmed by radiofrequency detector(s) located just outside the patient near his/her stomach. The radiofrequency detector(s) are then withdrawn and the external magnet 100, with its North Pole pointing towards the stomach, is brought closer to the patient. The capsule 10 will orientate itself so that the deflation mechanism at the second end 12 of the capsule 10 points towards the external magnet 100 as the south pole S of the deflation magnet 30 is attracted to the North pole of the external magnet 100. The external magnet 100 is then brought closer to a distance less than R3 (FIG. 7), at which point the deflation magnet 30 moves and accordingly displaces the small silicone plug 74, allowing air to leak out of the balloon 90. The deflated balloon 90 and the capsule 10 then travel through the pyloric sphincter and the rest of the alimentary canal before being passed out of the patient.

Because the balloon 90 may constrain the capsule 10 from coming into direct contact with the stomach wall, the magnetic force acting over R3 will be less. This means that the actuation force for the deflation mechanism should be less than that of the inflation mechanism. Yet, the fit of the plug 74 should be strong enough to resist the internal gas pressure.

Multiple Inflations

The opening of the septum or partition 80 may also be reversible, such that the operator of the external magnet 100 can exercise control over the extent of inflation. This may be achieved by having an elastic or magnetic force that returns the separator 84 seal to its original position and provides pressure to keep the hole 83 in the partition 80 closed.

Figure 8A:
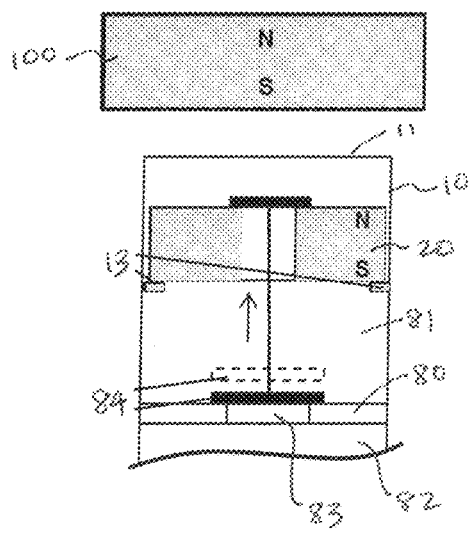
FIG. 8(a) is the intragastric device of FIG. 4 configured to allow multiple inflations.
Figure 8B:
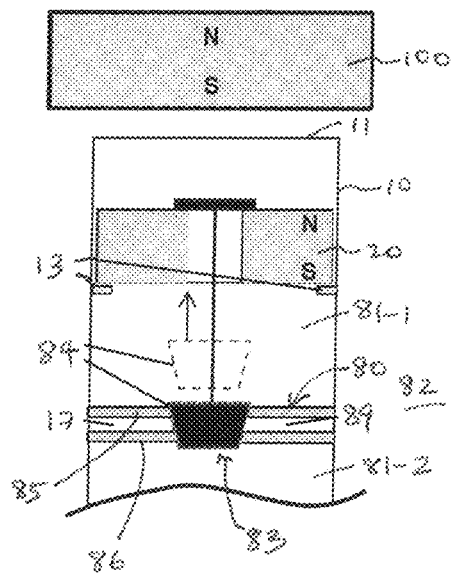
FIG. 8(b) is the intragastric device of FIG. 5 configured to allow multiple inflations.

For example, in the first and second exemplary embodiments described above with reference to FIGS. 2 to 6 where a deflation mechanism is provided that comprises the deflation magnet 30, if the external magnet 100 applied during inflation is removed after a predetermined period of time, the inflation magnet 20 will slide to its initial position due to the attraction force from the deflation magnet 30, and the inflation valve or through hole 83 in the partition 80 is closed. Then no more reaction is observed and there is no releasing of $CO_2$ or other gas until the valve or through hole 83 is opened. This allows for multiple inflation of the device 99 to inflate the balloon 90 to a desired volume. To allow multiple inflations for the device 90, the separator 84 may be designed to comprise a disc larger than the hole 83 as shown in FIG. 8(a) or a truncated cone as shown in FIG. 8(b) to ensure a good reseal after first opening of the hole 83.

Experiment

Real-time experiments were successfully carried out using the first embodiment of the intragastric device 99 as described above under Exemplary Embodiment 1, shown in FIGS. 2 to 4, 6(a) and 7. The device 99 was put inside a virtual stomach system EMS trainer 2068 from the chamberlain group, USA.

For the inflation phase, the external magnet 100 was held by the user. In this experiment, the south pole of the external magnet 100 was used for the inflation and its North pole was used for the deflation. When the south pole of the external magnet 100 approached the stomach, the capsule 10 automatically aligned along the axial direction of the external magnet 100. To open the inflation valve or through hole 83, the external magnet 100 was moved closer to the capsule 10 and then the inflation valve or through hole 83 was opened to mix the two chemicals stored separately in the first chamber 81 and the second chamber 82 together. Acid acetic and sodium bicarbonate were used as the acid and the base, respectively. After a period of time (around 1 min), the balloon 90 was completely inflated due to the increase of the CO2 gas.

To deflate the balloon, the north pole of the external magnet 100 was put towards the magnetic capsule or device 99. Once the external magnet 100 was moved closer to the device 99, the through opening 73 of the deflation valve was opened and after few seconds, the balloon 90 was completely deflated to its initial shape.

Exemplary Embodiment 3

Figure 9:
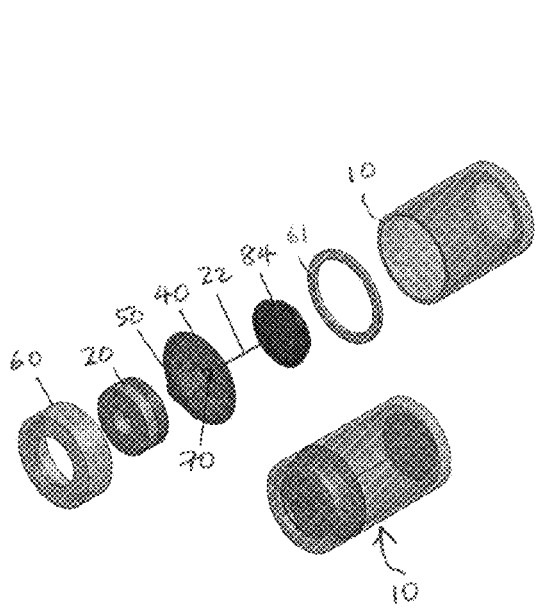
FIG. 9 is a schematic cross sectional view of a third exemplary embodiment of the intragastric device.
Figure 9:
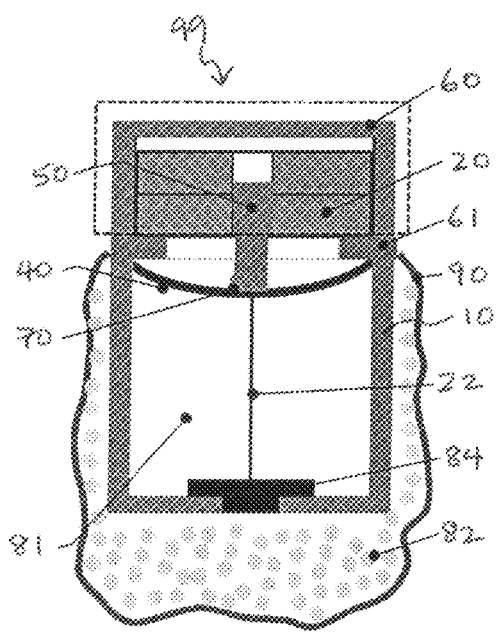

In this embodiment, as shown in FIG. 9, the partition 80 comprises the second end 12 of the capsule 10 so that the through hole 83 is in the second end 12 of the capsule 10. The first chamber 81 is thus defined by the side walls 15 of the capsule 10 and the second end 12 of the capsule. The second chamber 82 is defined by the balloon 90 and is one and the same as the expandable volume 98 of the balloon 90.

A flexible membrane 40 provided in the capsule 10 between the inflation magnet 20 and the first chamber 81. A perimeter of the flexible 40 membrane sealed with the capsule 10. The flexible membrane 40 is connected to the inflation magnet 20 via a biodegradable connector 50. The separator 84 is connected to the inflation magnet 20 via an adhesive connection 70 to the flexible membrane 40 as the inflation magnet 20 is now connected to the flexible membrane via the biodegradable connector 50. A portion 60 of the capsule 10 containing the inflation magnet 20 is connected to the rest of the capsule 10 via a biodegradable ring 61.

The surface materials for the capsule 10, the flexible membrane 40, the separator 84 and the connector 22 between the separator 84 and the flexible membrane 40 should be acid-resistant plastic or rubber materials like Polydimethylsiloxane (PDMS). The biodegradable connector 10 and biodegradable ring 61 may be made of an absorbable material like Chitosan, gelatin, polyglycolic acid, polylactic acid, Monocryl and polydioxanone, or a mixing material between PDMS and Chitosan, while the adhesive connection 70 may be either a plastics or silicon rubber material such as Ecoflex® or PDMS.

Figure 10:
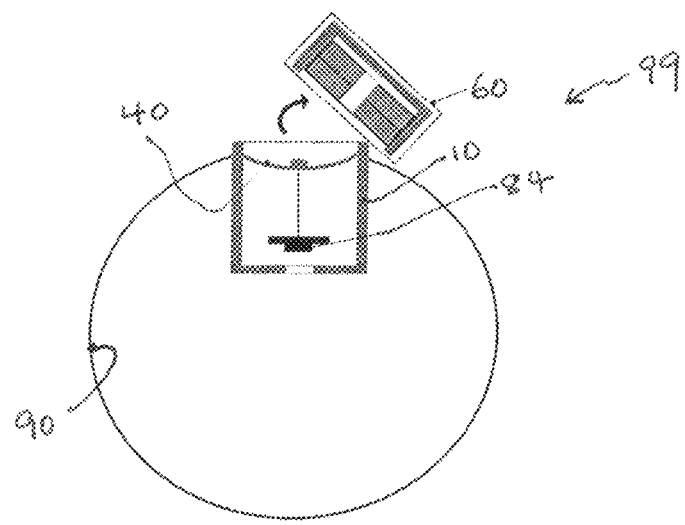
FIG. 10 is the intragastric device of FIG. 9 during detachment of a portion of the capsule containing the inflation magnet after inflation of the balloon.

The inflation magnet 20 and the portion 60 of the capsule 10 containing the inflation magnet 20 are configured to be detached from the rest of the capsule 10 upon biodegradation of the biodegradable connector 50 and the biodegradable ring 61. This is designed to take place after the balloon 90 has been inflated, as shown in FIG. 10.

Figure 11:
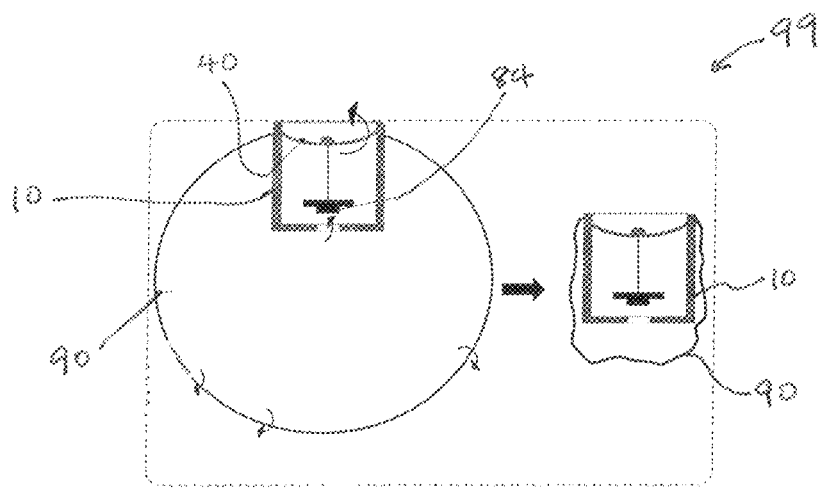
FIG. 11 is the intragastric device of FIG. 10 in a first exemplary embodiment of deflation of the balloon.

The whole balloon 90 can be designed to be automatically deflated after a predetermined time of treatment where the gaseous reaction product is diffused through the material of the balloon 90, as shown in FIG. 11. This may take place over the whole balloon 90 or partially through one or more semipermeable membranes provided in the balloon 90 through which the gas is leaked from the balloon 90 over a period of time. In such case, the balloon 90 can be made from biocompatible and acid resistant materials that prevent leakage of the gas from the balloon 90. Typical materials for this balloon 90 can be Typical materials can be PDMS or PDMS-coated highly stretchable silicone rubbers like Ecoflex or Dragon skin.

Figure 12:
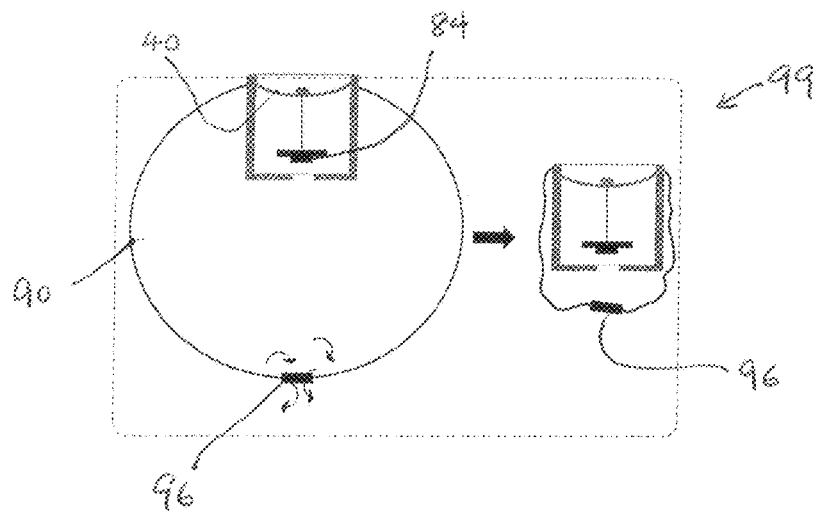
FIG. 12 is the intragastric device of FIG. 10 in a second exemplary embodiment of deflation of the balloon.

Alternatively, the whole balloon 90 may be made of a gas-resistant flexible material and the gas can be diffused via a deflation valve 96 provided in the material of the balloon 90, as shown in FIG. 12. Such a gas-resistant balloon 90 is preferably made of an elastic biocompatible material such as silicone elastomer or elastic materials like PDMS or medical Nylon or a thin layer of non-stretch reduced permeability packaging film EVAL provided by Kuraray, Japan.

The flexible membrane 40 may also be configured to allow passage of the gaseous product out of the device 99 over time. Typical materials for this flexible membrane 40 can be PDMS or PDMS-coated highly stretchable silicone rubbers like Ecoflex or Dragon skin.

Figure 13:
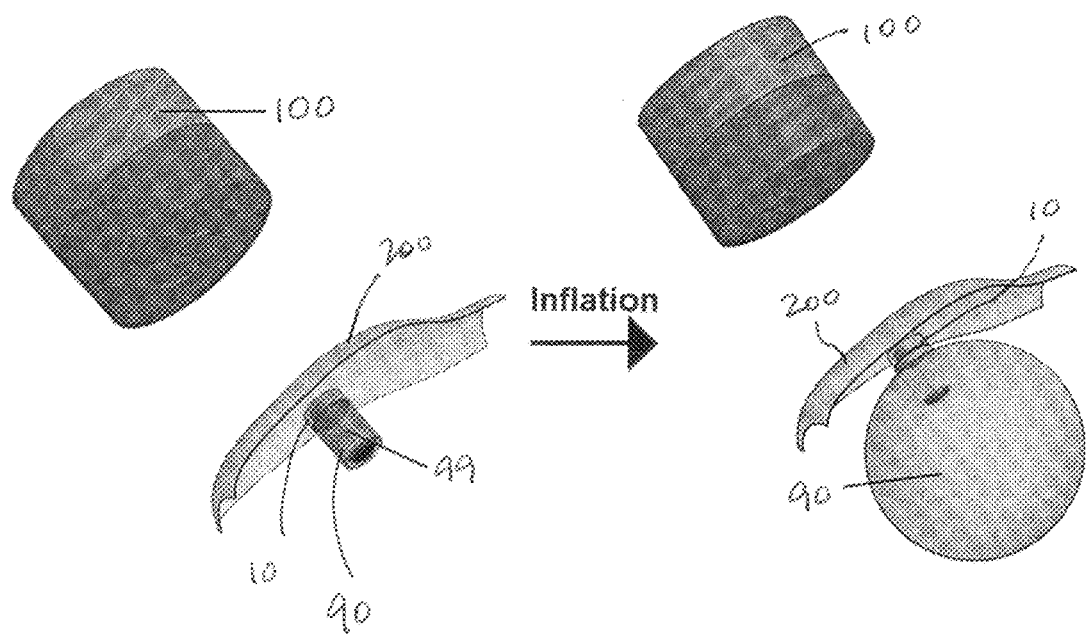
FIG. 13 is a perspective cutaway illustration of use of an external magnet to inflate the intragastric device in the stomach.

FIG. 13 shows the intragastric device 99 before and after inflation in a cutaway schematic illustration of the device 99 in the stomach 200 under the magnetic field of an external magnet 100. As can be seen, after inflation, the balloon 90 occupies a certain space in the stomach 200 and hence introduces the feeling of satiety so that the person would consume less food.

Further Embodiments

It should be understood that various combinations of the features in the different exemplary embodiments described above may be made in order to provide further different embodiments of the intragastric device 99.

Figures 14, 15, 16:
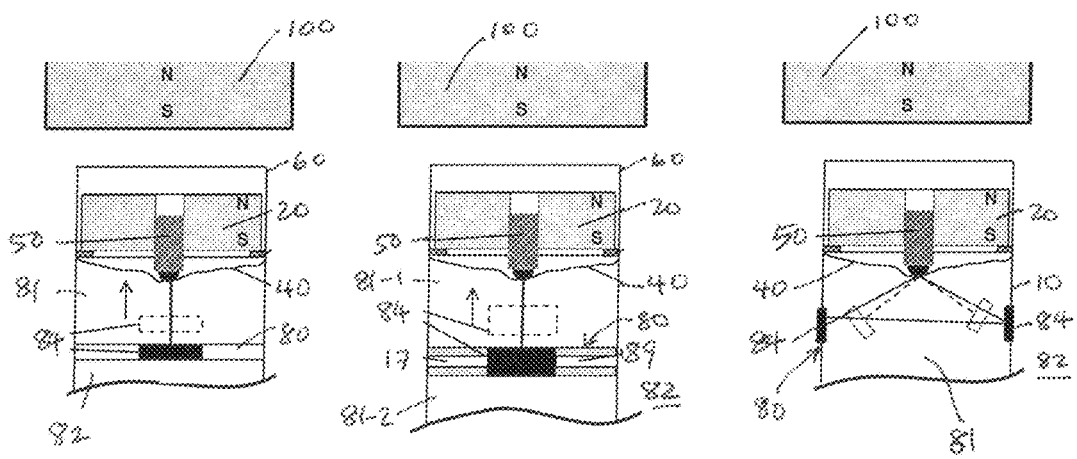
FIG. 14 is schematic cross sectional view of a further exemplary embodiment of the intragastric device.
FIG. 15 is schematic cross sectional view of another exemplary embodiment of the intragastric device.
FIG. 16 is schematic cross sectional view of an alternative exemplary embodiment of the intragastric device.

For example, FIGS. 14 and 15 show embodiments in which the intragastric device 99 of Exemplary Embodiment 1 and Exemplary Embodiment 2 described above are provided with the flexible membrane 40 and detachable inflation magnet 20 and portion 60 of the capsule 10 containing the inflation magnet 20 as described in Exemplary Embodiment 3.

FIG. 16 shows Exemplary Embodiment 3 modified so that the partition 80 comprises the side walls 15 of the capsule 10 so that a number of through holes 83 are provided in the side walls 15 of the capsule. The number of through holes 83 are sealed with a corresponding number of the separators 84 that are similarly connected to the inflation magnet 20 via a corresponding number of connectors 22 that are adhesively connected to the flexible membrane 40.

In an embodiment of use, multiple devices 99 can be swallowed for the treatment. For example, the subsequent device 99 can be administered every 2-3 hours from the first device 99. During gastric residence, the gas in the inflated balloon 90 will be diffused wholly through the balloon 90 wall or partially from the flexible membrane 40 if such is provided, and hence the balloon 90 will be automatically deflated. The deflated balloon 90 and capsule 10 are small enough to pass through the gastrointestinal tract for the entire intragastric device 99 to be naturally excreted after use.

Whilst there has been described in the foregoing description exemplary embodiments of the present invention, it will be understood by those skilled in the technology concerned that many variations and combinations in details of design, construction and/or operation may be made without departing from the present invention. For example, the septum or partition can be broken down on demand via the motive force provided by the inflation magnetic/inflation magnetophilic component interacting with the external inflation magnetic field and the reaction force from the gastrointestinal wall. Various applications of the motive force could include displacement of a section, or separation, perforation, destruction, comminution etc, thus allowing mixing of the reactants in the first and second chambers. The movement of chemicals may be throttled so as to achieve a controlled reaction, by means of a narrow opening in the septum or partition, or using a wicking material. Depending on the nature of the chemical reaction between the first and second chemicals, the reaction may be confined within the first chamber or the second chamber, or allowed to progress within the entirety of the expanding volume of the membrane or balloon. The reactants may be dispersed throughout different compartments of the device for optimal rate or completion of the reaction. In certain embodiments, the device may be made to carry pharmaceutical drugs to a target location. Once its location has been confirmed by the position sensing subcomponent, the motive force from the repurposed inflation mechanism is then used to either disperse the drug or inject it into the gastrointestinal lining. In certain embodiments, the device may be used for tissue biopsy. As the inflation process will cause the device to be braced against the gastrointestinal wall, this offers an interface at which tissue sampling may be conducted. The motive force of the inflation mechanism may be repurposed to slice off small bits of tissue, which are then stored within a self-sealing chamber.

REFERENCES

[1] O. G. Nieben, H. Harboe, Intragastric balloon as an artificial bezoar for treatment of obesity, Lancet, 1 (1982) 198-199.

[2] J. B. Wade, R. P. Hart, D. F. Kirby, P. R. Mills, An evaluation of the Garren-Edwards diet and behavior modification program, Group, 12 (1988) 172-178.

[3] C. H. Wahlen, B. Bastens, J. Herve, C. Malmendier, B. Dallemagne, C. Jehaes, S. Markiewicz, B. Monami, J. Weerts, The BioEnterics Intragastric Balloon (BIB): How to Use it, OBES SURG, 11 (2001) 524-527.

[4] P. Forestieri, G. D. De Palma, A. Formato, M. E. Giuliano, A. Monda, V. Pilone, A. Romano, S. Tramontano, Heliosphere® Bag in the Treatment of Severe Obesity: Preliminary Experience, OBES SURG, 16 (2006) 635-637.

[5] J.-M. Dumonceau, Evidence-based Review of the Bioenterics Intragastric Balloon for Weight Loss, OBES SURG, 18 (2008) 1611-1617.

The invention claimed is:

1. An intragastric device for weight management, the intragastric device comprising:
a capsule having a longitudinal axis, the capsule configured to be readily swallowed by a human person;
an inflation magnet provided within the capsule such that one of a north pole and a south pole of the inflation magnet is facing a first end of the capsule, the inflation magnet being displaced from the first end of the capsule, the inflation magnet configured to slideably engage the capsule during movement of the inflation magnet along the longitudinal axis, the inflation magnet configured to move towards the first end of the capsule during activation of the intragastric device by application of an inflation magnetic field externally to a user after the intragastric device has been swallowed by the user;
a first chamber configured to store a first chemical therein;
a second chamber configured to store a second chemical therein;
a partition configured to physically separate the first chamber from the second chamber, the partition having a through hole, the inflation magnet provided between the partition and the first end of the capsule, the first chamber defined within the capsule at least partially between the inflation magnet and the partition, the second chamber defined at least partially by the partition and the capsule;
a separator sealing the through hole in the partition before activation of the intragastric device, the separator being connected to the inflation magnet wherein movement of the inflation magnet towards the first end of the capsule moves the separator to unseal the through hole;
wherein fluid communication is established between the first chamber and the second chamber via the through hole when the through hole is unsealed to allow a chemical reaction between the first chemical and the second chemical;
a balloon secured to the capsule and collapsed against an outer surface of the capsule before activation of the intragastric device; and
an expandable volume defined at least partially by the balloon and the outer surface of the capsule, the expandable volume configured to expand when the balloon is inflated by a gaseous product of the chemical reaction.

2. The intragastric device of claim 1, wherein the second chamber and the expandable volume are one and the same.

3. The intragastric device of claim 2, wherein the partition comprises the second end of the capsule.

4. The intragastric device of claim 2, wherein the partition comprises a side wall of the capsule.

5. The intragastric device of claim 2, wherein the first chamber comprises a first portion defined between the inflation magnet and the partition and a second portion defined between the partition and a second end of the capsule, wherein the partition comprises a first layer having a first opening and a second layer having a second opening, the first opening and the second opening defining the through hole of the partition, the first layer and the second layer being spaced apart and defining a channel therebetween, the channel being in fluid communication with the second chamber via a channel opening in a side wall of the capsule.

6. The intragastric device of claim 5, wherein a deflation valve is provided at the second end of the capsule, the deflation valve allowing passage of the gaseous product out of the balloon.

7. The intragastric device of claim 6, wherein the deflation valve comprises a through opening in the second end of the capsule and a plug sealing the through opening before deflation of the intragastric device, the intragastric device further comprising a deflation magnet provided within the capsule and oriented in a same direction as the inflation magnet, the deflation magnet being displaced from the second end of the capsule, the deflation magnet configured to slideably engage the capsule during movement of the deflation magnet along the longitudinal axis, the deflation magnet configured to move towards the second end of the capsule during application of an inflation magnetic field externally to the user wherein movement of the deflation magnet causes removal of the plug from the through opening.

8. The intragastric device of claim 7, wherein the deflation magnet is connected to the plug via a flexible cable run over a pulley provided in the capsule, wherein movement of the deflation magnet towards the second end of the capsule pulls the plug into the capsule to unseal the through opening.

9. The intragastric device of claim 7, wherein the deflation magnet is provided with a bar extending towards the second end of the capsule, wherein movement of the deflation magnet towards the second end of the capsule results in the bar coming into contact with the plug and pushing the plug out of the capsule to unseal the through opening.

10. The intragastric device of claim 1, wherein the second chamber is defined within the capsule between the partition and a second end of the capsule, and wherein ventilation holes are provided in the capsule to establish fluid communication between the second chamber and the volume.

11. The intragastric device of claim 1, further comprising retaining stubs projecting from an inner surface of the capsule, the retaining stubs limiting extent of movement of the inflation magnet towards a second end of the capsule.

12. The intragastric device of claim 1, wherein the inflation magnet is connected to the separator via one of: a rigid rod and a flexible wire.

13. The intragastric device of claim 1, further comprising a flexible membrane provided in the capsule between the inflation magnet and the first chamber, a perimeter of the flexible membrane sealed with the capsule.

14. The intragastric device of claim 13, wherein the flexible membrane is connected to the inflation magnet via a biodegradable connector.

15. The intragastric device of claim 14, wherein a portion of the capsule containing the inflation magnet is connected to the rest of the capsule via a biodegradable ring, wherein the inflation magnet and the portion of the capsule containing the inflation magnet become detached from the rest of the capsule upon biodegradation of the biodegradable connector and the biodegradable ring.

16. The intragastric device of claim 15, wherein the separator is connected to the inflation magnet via an adhesive connection to the flexible membrane.

17. The intragastric device of claim 16, wherein flexible membrane allows passage of the gaseous product out of the balloon over time.

18. The intragastric device of claim 1, wherein the balloon allows passage of the gaseous product out of the balloon over time.

19. The intragastric device of claim 1, wherein the balloon comprises a deflation valve allowing passage of the gaseous product out of the balloon over time.

20. The intragastric device of claim 1, wherein the separator is configured to reseal the through hole in the partition when the externally applied inflation magnetic field is removed.

* * * * *